United States Patent [19]
Sugi et al.

[11] Patent Number: 6,090,940
[45] Date of Patent: Jul. 18, 2000

[54] METHOD FOR PRODUCING POTASSIUM OXONATE

[75] Inventors: Mitsuyo Sugi; Masami Igi, both of Osaka, Japan

[73] Assignees: Sumika Fine Chemicals Co., Ltd., Osaka; Taiho Pharmaceutical Co., Ltd., Tokyo, both of Japan

[21] Appl. No.: 09/307,179

[22] Filed: May 7, 1999

[30] Foreign Application Priority Data

May 11, 1998 [JP] Japan ................................. 10-127487

[51] Int. Cl.⁷ .................................................. C07D 251/30
[52] U.S. Cl. ............................................................ 544/223
[58] Field of Search ............................................. 544/223

[56] References Cited

FOREIGN PATENT DOCUMENTS 60-36463  2/1985  Japan .

OTHER PUBLICATIONS

Dr. Leroy B. Townsend et al, Nucleic Acid Chemistry, vol. 1, pp. 93–95 (1978).
J. Am Chem. Soc. vol. 77, pp. 1051–1052 (1955). Hartman et al.
M. Poje et al., Tetrahedron, 42(2) pp. 747–571 (1986).
M. Poje et al., Tetrahedron, 44(21) pp. 6723–6728 (1988).
H. Kaur et al., Chem.–Biol. Interact., 73(2–3) pp. 235–247 (1990).

*Primary Examiner*—John M. Ford
*Attorney, Agent, or Firm*—Birch, Stewart, Kolasch & Birch, LLP

[57] ABSTRACT

A method for producing potassium oxonate which comprises dissolving allantoin in an aqueous potassium hydroxide solution or an aqueous potassium carbonate solution, and oxidizing said allantoin with an alkali metal hypohalogenite in the presence of potassium iodide is provided and, according to the method, potassium oxonate can be efficiently produced without requiring a manganese compound which may entail environmental pollution.

7 Claims, No Drawings

METHOD FOR PRODUCING POTASSIUM OXONATE

BACKGROUND OF THE INVENTION

1. Field of the Invention

The present invention relates to a method for producing potassium oxonate. More particularly, it relates to a method for producing potassium oxonate without using compounds having an adverse effect on the earth's environment.

2. Prior Art

Potassium oxonate is a compound useful in alleviating side effects resulting from the use of a 5-fluorouracil type anticancer agent and digestive tract disorders such as diarrhea and stomatitis, and is effective as a formulating ingredient of the 5-fluorouracil type anticancer agent.

Potassium oxonate has been conventionally produced in the following manner: allantoin or uric acid is dissolved in an aqueous potassium hydroxide solution, then an oxidative decomposition is carried out with oxidizing agents such as potassium permanganate, manganese dioxide and hydrogen peroxide, followed by removal of insoluble matter, and performing a treatment such as acid precipitation. [JP-A-60-36463, Journal of American Chemical Society [J. Am. Chem. Soc.] 77, 1051–1052 (1955)].

However, such a conventional method, which uses potassium permanganate and manganese dioxide as oxidizing agent, may adversely affect the environment. Accordingly, the development of a production method for potassium oxonate not using these compounds has been desired in recent years. Conventional methods which use hydrogen peroxide as an oxidizing agent also has a disadvantage in that the yield of the resulting potassium oxonate is extremely low.

As a method for producing potassium oxonate without using manganese compounds, there has been proposed a method in which biuret and potassium ethyl oxalate undergo condensation and cyclization in the presence of potassium ethoxide catalyst in ethanol [Nucleic Acid Chemistry [Nucl. Acid Chem.] 1, 93–95, (1978)].

However, the method requires the use of the expensive compound, biuret and potassium ethyl oxalate, as raw materials. Thus, this is not a preferable method in terms of cost efficiency.

The present invention has been achieved with a view of solving the foregoing problems.

SUMMARY OF THE INVENTION

An object of the present invention to provide a method capable of producing potassium oxonate with high cost efficiency on an industrial scale without adversely affecting the Earth's environment.

Accordingly, the present invention provides a method for producing potassium oxonate which comprises oxidizing allantoin, which is dissolved in an aqueous potassium hydroxide solution or an aqueous potassium carbonate solution, with an alkali metal hypohalogenite in the presence of potassium iodide.

DETAILED DESCRIPTION OF THE PREFERRED EMBODIMENTS

According to the method of the present invention, potassium oxonate is preferably produced in the following manner. First, allantoin is dissolved in an aqueous potassium hydroxide solution or an aqueous potassium carbonate solution, and then the allantoin is oxidized by an aqueous solution of alkali metal hypohalogenite in the presence of potassium iodide.

As indicated above, in the present invention, first, allantoin is dissolved in an aqueous potassium hydroxide solution or an aqueous potassium carbonate solution.

Allantoin may be added to an aqueous potassium hydroxide solution or an aqueous potassium carbonate solution. Alternatively, allantoin and potassium hydroxide or potassium carbonate may be added and dissolved in water simultaneously, or potassium hydroxide or potassium carbonate may be added to an aqueous dispersion of allantoin to dissolve the allantoin, as long as the temperature is controlled so as to not cause the decomposition of allantoin.

In general, the concentration of potassium hydroxide in the aqueous potassium hydroxide solution is preferably in the range of approximately 1 to 50%. Also, in general, the concentration of potassium carbonate in the aqueous potassium carbonate solution is preferably in the range of approximately 1 to 50%.

Generally, allantoin may be properly used in an amount in the range of approximately 1 to 400 parts by weight per 100 parts by weight of potassium hydroxide or potassium carbonate, although the ratio of allantoin to potassium hydroxide or potassium carbonate has no specific restriction.

When temperature of the aqueous potassium hydroxide solution or the aqueous potassium carbonate solution in which allantoin is to be dissolved is too low, longer periods of time are required for dissolving the allantoin. Hence, the temperatures of the solutions should preferably be at about 0° C. or higher. On the other hand, when the temperatures of these solutions are too high, a decomposition of allantoin dissolved in the alkaline aqueous solution is observed. Hence, the temperatures of these solutions should preferably be at about 10° C. or lower.

In the present invention, potassium iodide is also added to the aqueous potassium hydroxide solution or aqueous potassium carbonate solution wherein the allantoin has been dissolved or is to be dissolved. The potassium iodide may be added to the solution simultaneously with the addition of the allantoin. Allantoin, potassium hydroxide or potassium carbonate and the potassium iodide may be added and dissolved in water in any order, or simultaneously, as long as the temperature is controlled so as to not cause a decomposition of allantoin.

One of the main characteristics of the present invention resides in the use of potassium iodide. That is, the use of potassium iodide gives an excellent effect of an improved reaction rate due to ion exchange and an enhancement in oxidizing power.

In general, potassium iodide is preferably used in an amount of about 0.01 mole or more per mole of allantoin from the viewpoint of increasing the reaction rate, while it is preferably used in an amount of about 0.1 mole or less per mole of allantoin from the viewpoint of cost efficiency and controllability of the reaction.

Before conducting the subsequent oxidation reaction, the temperature of the resulting aqueous solution containing allantoin, potassium iodide and potassium hydroxide or potassium carbonate is preferably at about 0° C. or higher from the viewpoint of the solubility of the allantoin and the potassium iodide, while it is preferably at about 10° C. or lower from the viewpoint of the stability of allantoin in the alkaline aqueous solution.

After adding potassium iodide to the solution, the allantoin is oxidized by an alkali metal hypohalogenite in the solution.

For carrying out the oxidation of the allantoin with an alkali metal hypohalogenite, for example, an alkali metal hypohalogenite is added to the aqueous solution in which allantoin, potassium iodide and potassium hydroxide or potassium carbonate are dissolved (hereinafter, referred to as "method A"); or a halogen is introduced into the aqueous solution in which allantoin, potassium iodide and potassium hydroxide or potassium carbonate are dissolved (hereinafter, referred to as "method B"). When a halogen is introduced into the aqueous solution, an alkali metal hypohalogenite is generated in the solution.

Examples of the alkali metal hypohalogenite to be used in the method A include potassium hypochlorite, sodium hypochlorite, potassium hypobromite, sodium hypobromite, potassium hypoiodite and sodium hypoiodite. Among these compounds, potassium hypochlorite, potassium hypobromite and sodium hypochlorite are preferably used in the present invention. The alkali metal hypohalogenite is preferably added as an aqueous solution thereof. When the alkali metal hypohalogenite is added as an aqueous solution thereof, in general, the concentration of the alkali metal hypohalogenite in the aqueous solution is preferably in the range of approximately 5 to 20% by weight.

In general, the amount of alkali metal hypohalogenite to be used is preferably at the stoichiometric amount, i.e., 1 mole or more per mole of allantoin. Also, it is preferably at 4 mole or less from the viewpoint of promoting the oxidation reaction of allantoin with the alkali metal hypohalogenite in the alkaline aqueous solution and reducing the amount of waste liquid after completion of the reaction.

When the aqueous solution of alkali metal hypohalogenite is added thereto, the temperature of the solution is preferably at about 0° C. or more from the viewpoint of enhancing the reactivity. Also, it is preferably at about 10° C. or less from the viewpoint of the stability of allantoin in the alkaline aqueous solution and the controllability of exothermic heat on oxidation of allantoin in the solution.

Examples of halogen to be used in the method B include a chlorine, a bromine, and an iodine. Among these halogens, the chlorine and bromine are preferably used in the present invention.

When the halogen is a gas, the halogen can be bubbled into the solution. When the halogen is a liquid, the halogen can be properly added dropwise to the solution. When the halogen is a solid, the halogen can be properly added and dissolved in the solution.

In general, the amount of halogen to be used is preferably at the stoichiometric amount of the oxidation reaction, i.e., about 2 mole or more per mole of allantoin. Also, it is preferably at about 8 mole or less from the viewpoint of facilitating the treatment after completion of the reaction and cost efficiency. When the halogen is introduced to the solution in the Method B, the temperature is preferably at about 0° C. or more from the viewpoint of enhancing the reactivity, and it is preferably at about 5° C. or less from the viewpoint of enhancing the stability of allantoin in the alkaline aqueous solution and the stability of alkali metal hypohalogenite generated by the introduction of the halogen.

After the addition of an alkali metal hypohalogenite in the method A, or the introduction of a halogen in the method B, the temperature of the resulting solution is preferably at about 15° C. or higher from the viewpoint of enhancing the reaction rate, while it is preferably at about 30° C. or lower from the viewpoint of facilitating the control of the reaction.

Thereafter, the resulting reaction solution is neutralized and cooled to obtain potassium oxonate as crystaline substance. Examples of the compound which can be used for neutralizing the reaction solution include organic acids such as formic acid, acetic acid, propionic acid, and oxalic acid; and mineral acids such as hydrochloric acid and sulfuric acid. In general, the pH after the neutralization is preferably in the range of approximately 5 to 6.

The obtained crystaline potassium oxonate is preferably, if required, washed with cold water, cold acetone, or the like, followed by drying.

As described above, according to the production method of the present invention, potassium oxonate can be efficiently produced without requiring a manganese compound which may entail environmental pollution.

The present invention will be described in more detail by way of examples, which should not be construed as limiting the scope of the present invention.

EXAMPLE 1

In a flask with a volume of 500 ml, 271 g of 16.6% aqueous potassium hydroxide solution was added. Then, 15.8 g of allantoin and 0.79 g of potassium iodide were added thereto and dissolved, while keeping the internal temperature in the range of 0 to 10° C. Thereafter, 32.0 g of bromine was added dropwise thereto at such a rate as to keep the internal temperature at 2 to 5° C. for approximately 2.5 hours.

After completion of the addition of bromine, the internal temperature was raised to 20° C., followed by stirring for approximately 22 hours. Then, the reaction solution was neutralized with 21.5 g of acetic acid to a pH of approximately 6 to precipitate crystals.

Subsequently, the reaction solution was cooled to approximately 5° C., followed by stirring for 2 hours. Thereafter, the crystals were filtered off, and the obtained crystals were washed with 66 ml of cold water, and 22 ml of cold acetone, successively.

Then, the crystals were dried to obtain 13.7 g of potassium oxonate. The yield of the resulting potassium oxonate from allantoin was 70%.

The physical properties of the obtained potassium oxonate are shown below.

IR (KBr) ν ($cm^{-1}$): 3170, 1750, 1720, 1655, 1622, 1490, 1395, 780

$^{13}$C-NMR (100 MHz, heavy water) δ (ppm): 160.06, 164.35, 158.63

Elemental analysis: theoretical values C 24.62%, H 1.03%, N 21.53% observed values C 24.73%, H 1.15%, N 21.83%

EXAMPLE 2

Into a flask with a volume of 500 ml, 15.8 g of allantoin, 118.5 ml of water, 13.9 g of 85% potassium hydroxide and 0.79 g of potassium iodide were added, followed by mixing and dissolution while keeping the inner temperature at 0 to 5° C. Then, 181.1 g of a commercially available aqueous solution of potassium hypochlorite (chlorine content in the solution: 5 to 7%) was added dropwise thereto over approximately 2.5 hours while keeping the internal temperature at 2 to 5° C.

After completion of the addition of the aqueous solution of potassium hypochlorite, the internal temperature was raised to 25° C., followed by stirring for approximately 18.5 hours. Then, the reaction solution was neutralized with 9.17 g of acetic acid to a pH of approximately 6 to precipitate crystals. Subsequently, the reaction solution was cooled to approximately 5° C., followed by stirring for 2 hours. Thereafter, the crystals were filtered off, and the obtained crystals were washed with 66 ml of cold water, and 22 ml of cold acetone, successively, and dried to obtain 8.6 g of potassium oxonate. The yield of the resulting potassium oxonate from allantoin was 44%. Further, the IR of the resulting potassium oxonate was found to be the same as in the example 1.

EXAMPLE 3

Into a flask with a volume of 500 ml, 15.8 g of allantoin, 118.5 ml of water, 13.9 g of 85% potassium hydroxide and 0.79 g of potassium iodide were added, followed by mixing and dissolution, while keeping the internal temperature at 0 to 5° C. Then, 132.9 g of a commercially available aqueous solution of sodium hypochlorite (chlorine content in the solution: approximately 5%) was added dropwise thereto over approximately 2.5 hours while keeping the internal temperature at 2 to 5° C.

After completion of the addition of the aqueous solution of sodium hypochlorite, the internal temperature was raised to 25° C., followed by stirring for approximately 23 hours. Then, the reaction solution was neutralized with 11.28 g of acetic acid to a pH of approximately 6 to precipitate crystals. Subsequently, the reaction solution was cooled to approximately 5° C., followed by stirring for 1 hour. Thereafter, the crystals were filtered off, and the obtained crystals were washed with 66 ml of cold water, and 22 ml of cold acetone, successively, and dried to obtain 7.8 g of potassium oxonate. The yield of the resulting potassium oxonate from allantoin was 40%. The IR of the resulting potassium oxonate was found to be the same as in the example

EXAMPLE 4

Into a flask with a volume of 500 ml, 271 g of 16.6% aqueous solution of potassium hydroxide was added, which was then cooled to 0 to 10° C. Then, 15.8 g of allantoin and 0.79 g of potassium iodide were added thereto, followed by dissolution, while keeping the internal temperature at 0 to 5° C. Thereafter, 14.2 g of chlorine gas was bubbled into the alkaline solution of allantoin over approximately 2.5 hours while keeping the internal temperature at 2 to 5° C.

After completion of the bubbling of chlorine gas, the internal temperature was raised to 20° C., followed by stirring for approximately 22 hours. Then, the reaction solution was neutralized with 21.5 g of acetic acid to a pH of approximately 6 to precipitate crystals.

After ice-cooling, the solution was stirred for 2 hours. Thereafter, the crystals were filtered off, and the obtained crystals were washed with 66 ml of cold water, and 22 ml of cold acetone, successively, and dried to obtain 13.5 g of potassium oxonate. The yield of the resulting potassium oxonate from allantoin was 69%. The IR of the obtained potassium oxonate was found to be the same as in the example

EXAMPLE 5

Into a flask with a volume of 500 ml, 15.8 g of allantoin, 118.5 ml of water, 13.9 g of 85% potassium hydroxide and 0.79 g of potassium iodide were added, followed by mixing and dissolution, while keeping the internal temperature at 0 to 5° C. Then, 132.9 g of 10% aqueous solution of potassium hypobromite which has been previously prepared by adding dropwise bromine into a cold potassium hydroxide solution was added dropwise thereto over approximately 2.5 hours while keeping the internal temperature at 2 to 5° C.

After completion of the addition of the aqueous solution of potassium hypobromite, the internal temperature was raised to 25° C., followed by stirring for approximately 23 hours. Then, the obtained reaction solution was neutralized with 11.28 g of acetic acid to a pH of approximately 6 to precipitate crystals.

The solution in which crystallization occurred was cooled to approximately 5° C., followed by stirring for 1 hour. Thereafter, the resulting crystals were filtered off, washed with 66 ml of cold water, and 22 ml of cold acetone, successively, and dried to obtain 12.7 g of potassium oxonate. The yield of the resulting potassium oxonate from allantoin was 65%. The IR of the resulting potassium oxonate was found to be the same as in the example 1.

COMPARATIVE EXAMPLE 1

Into a flask with a volume of 500 ml, 15.8 g of allantoin, 118.5 ml of water, 13.9 g of 85% potassium hydroxide, 0.79 g of potassium iodide and 11.9 g of potassium bromide were added, followed by mixing and dissolution, while keeping the internal temperature at 0 to 5° C. Then, 9.7 g of 35% aqueous hydrogen peroxide solution was added dropwise thereto over approximately 2 hours, while keeping the internal temperature at 2 to 5° C.

After completion of the addition of the aqueous hydrogen peroxide solution, the internal temperature was raised to 25° C. The resulting solution was stirred for approximately 23 hours, and further stirred for approximately 2.5 hours at 35° C. Then, 0.83 g of iron(II) sulphate heptahydrate was added thereto at 25° C., followed by stirring for 3 hours at the same temperature. Further, 9.7 g of 35% aqueous hydrogen peroxide solution was added to the reaction solution, followed by stirring for approximately 25 hours. Then, the resulting reaction solution was neutralized with 6.85 g of acetic acid to a pH of approximately 6 to precipitate crystals. Thereafter, the obtained crystals were cooled to approximately 5° C., followed by stirring for 1 hour. Then, the crystals were filtered off, and the obtained crystals were washed with 10 ml of cold water, and 10 ml of cold acetone, successively, and dried to obtain 0.39 g of potassium oxonate. The yield of the resulting potassium oxonate from allantoin was 2%

According to the method for producing potassium oxonate of the present invention, potassium oxonate can be produced on an industrial scale with economical efficiency without using compounds which may adversely affect the Earth's environment.

What is claimed is:

1. A method for producing potassium oxonate which comprises oxidizing allantoin, which is dissolved in an aqueous potassium hydroxide solution or an aqueous potassium carbonate solution, with an alkali metal hypohalogenite in the presence of potassium iodide.

2. A method for producing potassium oxonate according to claim 1, wherein an alkali metal hypohalogenite is added to the aqueous solution in which allantoin, potassium iodide and potassium hydroxide or potassium carbonate are dissolved.

3. A method for producing potassium oxonate according to claim 1, wherein a halogen is introduced into the aqueous solution in which allantoin, potassium iodide and potassium hydroxide or potassium carbonate are dissolved.

4. A method for producing potassium oxonate according to claim 2, wherein the alkali metal hypohalogenite is potassium hypochlorite, potassium hypobromite or sodium hypochlorite.

5. A method for producing potassium oxonate according to claim 3, wherein said halogen is a chlorine, a bromine, or an iodine.

6. A method for producing potassium oxonate according to claim 2, wherein the alkali metal hypohalogenite is added at a temperature of 0° C. to 10° C. and the oxidization of the allantoin is carried out at a temperature of 15° C. to 30° C.

7. A method for producing potassium oxonate according to claim 3, wherein the halogen is introduced at a temperature of 0° C. to 5° C. and the oxidization of the allantoin is carried out at a temperature of 15° C. to 30° C.

* * * * *